United States Patent [19]
McLean et al.

[11] Patent Number: 5,861,481
[45] Date of Patent: Jan. 19, 1999

[54] PEPTIDE LUNG SURFACTANTS AND THERAPEUTIC COMBINATIONS

[75] Inventors: Larry R. McLean, Wyoming; J. Vincent Edwards, Cincinnati, both of Ohio

[73] Assignee: Merrell Pharmaceuticals Inc., Cincinnati, Ohio

[21] Appl. No.: 855,740

[22] Filed: May 8, 1997

Related U.S. Application Data

[63] Continuation of Ser. No. 574,980, Dec. 19, 1995, abandoned, which is a continuation of Ser. No. 358,650, Dec. 19, 1994, abandoned, which is a continuation of Ser. No. 77,801, Jun. 21, 1993, abandoned, which is a continuation-in-part of Ser. No. 922,279, Jul. 29, 1992, abandoned.

[51] Int. Cl.$^6$ .............................. A61K 38/00; C07K 5/00; C07K 7/00
[52] U.S. Cl. .............................. 530/330; 530/402; 514/18
[58] Field of Search .................................... 530/330, 402; 514/18

[56] References Cited

U.S. PATENT DOCUMENTS 4,861,756   8/1989   Jackson ..................................... 514/11

FOREIGN PATENT DOCUMENTS 0348967   1/1990   European Pat. Off. .......... C07K 7/00
0529568   8/1992   European Pat. Off. .......... C07K 5/08

OTHER PUBLICATIONS

McLean, et al. Biochemica et Biophysica Acta 1167:289–295 (1993).
McLean, et al., Am. Rev. Respir Dis vol. 147:4622–465 (1993).
McLean, et al., Biochimica et Biophysica Acta 1166:31–38 (1993).
McLean, et al., Biochemistry vol. 30(1):31–37 (1991).
McLean, et al., Biochimica et Biophysica Acta 1167:289–95 (1993).
Unpublished article.
Cochrane, et al., Science, vol. 254:566–68 (1991).
Waring, et al., Peptide Research 2(5):308–313 (1989).
Travis, Am. Rev. Respir. Dis. 135:773–774 (1987).
Heffner, et al., Am. Rev. Respir. Dis 140:531–554 (1989).
McLean, et al., American Physiological Society, pp. L292–L300 (1992).
McLean, et al., Am. Rev. Respir. Dis., vol. 147:462–465 (1993).
McLean, et al., Biochimica et Biophysica Acta, 1166:31–38 (1993).
McLean, et al., Journal of Pharma. and Exp. therapeutics, vol. 266(2):551–556 (1993).
Fanger, et al., J. Cellular Biochemistry, Supplement 15B, Jan. 18–24, 1991, p. 123.
Cochrane, et al., "Pulmonary Surfactant Protein B (SP–B): Structure–Function Relationships", Science, vol. 254:566–568 (1991).
Waring, et al., "Synthetic Amphipathic Sequences of Surfactant Protein–B Mimic Several Physicochemical and In Vivo Properties of Native Pulmonary Surfactant Proteins", Peptide Research 2(5):308–313 (1989).
McLean, et al., "Role of the Hydrophobic Face of Amphipathic Alpha–Helical Peptides in Synthetic Pulmonary Surfactants", The Journal of Pharmacology and Experimental Therapeutics, vol. 266, No. 2, pp. 551–266 (1993).
Travis, Am. Rev. Respir. Dis. 135:773–774 (1987).
Heffner, et al., Am. Rev. Respir. Dis 140:531–554 (1989).
McLean, et al., American Physiological Society, pp. L292–L300 (1992).

*Primary Examiner*—Avis M. Davenport
*Attorney, Agent, or Firm*—T. Helen Payne

[57] ABSTRACT

Synthetic pulmonary surfactant consisting of a complex of a polypeptide of 3–4 amino acid residues having alpha-helical structure and a covalently bound long chain acyl group. The peptides are useful when consisting of one or more associated lipids in combination in conditions associated with respiratory distress.

16 Claims, 1 Drawing Sheet

Figure 1 succinyl-Leu-Leu-Glu-Lys-Leu-Leu-Glu-Trp-Leu-Lys-NH$_2$

Figure 2

Palmityl-Glu-Trp-Ala-Lys-NH$_2$

PEPTIDE LUNG SURFACTANTS AND THERAPEUTIC COMBINATIONS

CROSS-REFERENCE TO RELATED APPLICATION

This is a continuation of application Ser. No. 08/574,980, filed Dec. 19, 1995 now abandoned, which is a continuation of application Ser. No. 08/358,650, filed Dec. 19, 1994, now abandoned, which is a continuation of application Ser. No. 08/077,801, filed Jun. 21, 1993, now abandoned, which is a continuation-in-part of application Ser. No. 07/922,279, filed Jul. 29, 1992, now abandoned, which is herein incorporated by reference.

FIELD OF THE INVENTION

This invention relates to the synthesis of a series of tri- and tetra-polypeptides whose sequence is unrelated to the sequences of proteins of known mammalian lung surfactants, the preparation of mixtures of these polypeptides with hydrophobic extensions, and the method for production of the same and pharmaceutical compositions which are effective in the treatment of mammalian respiratory distress syndrome.

BACKGROUND OF THE INVENTION

Infantile respiratory distress syndrome (RDS) is a leading cause of death in the first 28 days of life. It strikes 1 in 100 babies worldwide and about 10 percent die. The syndrome rarely occurs in term infants but is generally associated with immaturity and in low-birth weight (under 2 kg). Adult RDS shows similar clinical characteristics and pathophysiology as the infantile disease and is managed in the intensive care facility in a similar fashion. The adult disease has diverse etiologies and results from lung insults such as diffuse infections, aspiration of the gastric contents or water, inhalation of irritants andtoxins and pulmonary edema arising from such sources as narcotic overdose. RDS is correlated with an absence or dysfunction of the lung surfactant which coats the alveoli of the lungs where gas exchange occurs.

Lung surfactant is composed primarily of lipid (90%) and contains a minor component of various proteins (10%). The primary lipid type is phospholipid which constitutes 97% of the lipid. 80% of this phospholipid is phosphatidylcholine (PC) and 10% is phosphatidyglycerol (PG). 70–80% of the phospholipid acyl chains are saturated and 85–90% of these are 16-carbons in length. The major lipid is dipalmitoylphosphatidylcholine (DPPC). The protein component of lung surfactant is also heterogeneous but more poorly characterized. The major protein is ~32 kd and its sequence has been predicted from its cDNA (White et al. (1985) *Nature* 317, 361–363) and it has been cloned (Floros, et al. Journal of Biological Chemistry (1985) 260, 495–500). Minor proteins of lower molecular weight have also been isolated and several sequences have been reported (Warr, et al. (1987) *Proceedings of the National Academy of Sciences USA* 82, 7915–7919; Glasser, et al. (1988) *Journal of Biological Chemistry* 263, 9; Johansson, et al. (1988) *FEBS Letters.* 232, 61–64; Glasser, et al. (1987) *Proceedings of the National Academy of Sciences USA* 84, 4007; Revak, et al. (1988) *Journal of Clinical Investigation* 81, 826–833).

Infantile RDS has been treated with animal lung lavages (Smyth, et al. (1983) *Pediatrics* 71, 913–917; McCord, et al. (1988) *Arch. Dis. Child.* 63, 10–16) and human lung surfactant obtained from human amniotic fluid (Hallman, et al. (1983) *Pediatrics* 71, 473–482; (1985) *J. Pediatr.* 106, 963–969; Merritt, et al. (1986) *N. Enql. J. Med.* 13, 785–790) with considerable success. Cow lung lavages extracted with organic solvents and mixed with synthetic lipids are also effective (Fujiwara, et al. (1980) *Lancet* 1, 55–59; Noach, et al. (1986) *Eur. J. Respir. Dis.* 69, 321–335; Kwong, et al. (1985) *Pediatrics* 76, 585–592; Enhorning, et al., (1985) *Pediatrics* 76, 145–153; Shapiro, et al. (1985) *Pediatrics* 76, 593–599; Gitlin, et al. (1987) *Pediatrics* 79, 31–37; Raju, et al. (1987) *Lancet* 1, 651–656; Halliday, et al (1984) *Lancet* 1, 476–478). However, pure synthetic mixtures have not consistently been shown to be active (Morley, et al., (1981) *Lancet* 1, 64–68; Ten Centre Study Group (1987) *Br. Med. J.* 294, 991–996; Milner, et al. (1983) *Arch. Dis. Child.* 58, 458–460; Milner, et al. (1983, *ibid* 59, 369–371; and Wilkinson, et al. (1985) *Lancet* 2, 287–291). Only a few clinical studies using surfactants in adult RDS are known, i.e., (Lochman, et al., (1988) *Adv. Exp. Med. Biol.* 222, 511–517), however, the potential value of such therapy has been indicated in the literature (van Golde, et al. *Physiol. Rev.* 68, 374–455).

Although limited success with pure lipid mixtures has been reported, it appears that a protein component of lung surfactant dramatically improves activity, such as is observed with natural lung surfactants (Hall. et al., *Am. Rev. Rspir. Dis.* (1992) 145, 24–30). One approach is to use genetically engineered proteins with sequences based on the amino acid sequences predicted from the cDNA of the lung surfactant proteins. An alternative method, which is the subject of the present invention is to synthesize peptides with physical properties suited to the function of lung surfactant when in combination with defined lipid components, but with sequences unrelated to the sequences of proteins isolated from lung surfactant.

The present invention is concerned with short peptides of 3 to 4 amino acids having an N-acyl group and compositions comprising a mixture of synthetic polypeptides and lipids effective in treating RDS. The synthetic polypeptides have unique sequences which are not found in the sequences of the mammalian proteins isolated from lung lavages. The polypeptides may be used singly in mixtures with lipid or in combination in mixtures of lipid. The polypeptide comprises a minor component of the surfactant mixture.

Recently it was demonstrated that of the several classes of lipid-binding peptides, having mixtures of an amphipathic α-helical peptide with about 10–24 amino acids, with dipalmitoylphosphatidylcholine (DPPC) were effective in restoring quasi-static lung compliance in vitro and gas exchange In vivo in lavaged lungs. The present invention has significantly decreased the size of the peptide required to only 3 to 4 amino acids by modifications of the amino and carboxy terminal.

Figure 1:
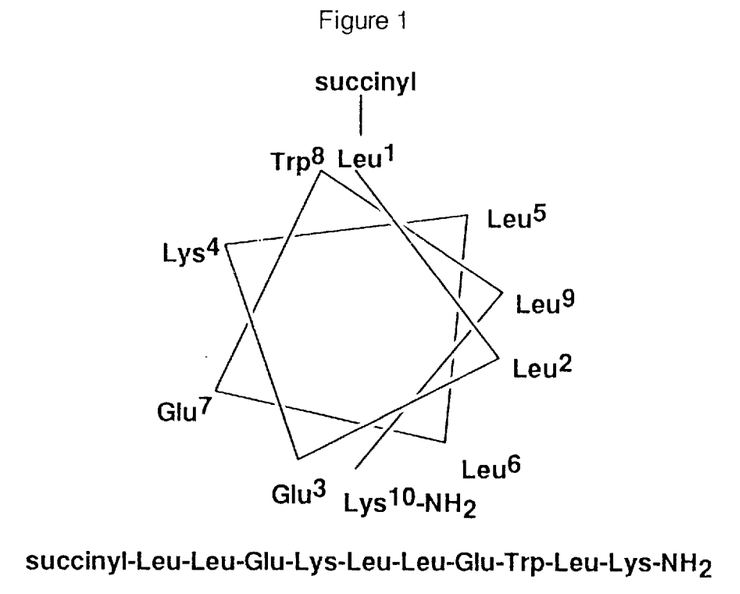
FIG. 1 is a helical wheel representation of a ten-residue peptide surfactant used to develop a model for short peptides. The view is down the barrel of the helix and the side chains of the residues are indicated in their positions relative to the axis of the helix. The hydrophobic face includes the residues to the right in the drawing which are $Trp^8$, $Leu^1$, $Leu^5$, $Leu^9$, $Leu^2$, $Leu^6$. The hydrophilic face includes the charged residues $Lys^4$, $Glu^7$, $Glu^3$, $Lys^{10}$.
Figure 2:
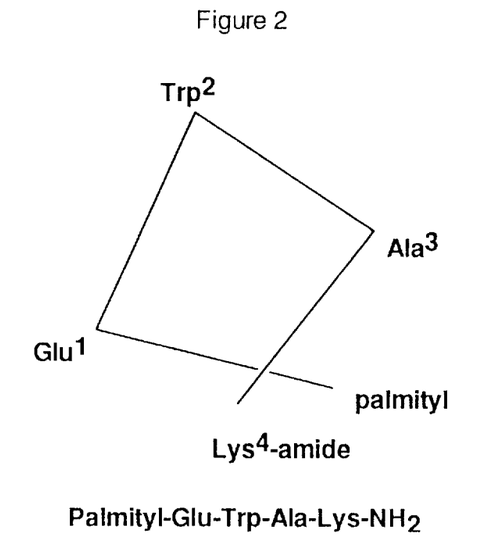
FIG. 2 is an example of a tetrapeptide designed on the basis of a single turn of the helical wheel projection of the ten-residue peptide shown in FIG. 1. The hydrophobic face of the FIG. 1 peptide has been replaced by $Trp^2$, $Ala^3$, palmityl which present a sufficient hydrophobic face to anchor the peptide to lipid. The hydrophilic charged face has been replaced by $Glu^1$, $Lys^4$.

A helical wheel representation of an amphipathic α-helical ten-residue peptide (for description of the amphipathic α-helical peptide see McLean, L. R. et al. *Biochem.,* 1991, 30, 31) is used to develop a model for three and four residue peptides. When looking down the barrel of the α-helix, the side chains of the residues indicate a hydrophobic face and a hydrophilic face on the helix. A four residue peptide represents a single turn of this α-helix with the required hydrophobic and hydrophilic face present. A three residue peptide represents a contricted turn of the α-helix with the hydrophobic and hydrophilic face still present.

The chemical composition of the present invention is novel with regard to the short peptide component of 3–4 amino acids adjoined to an acyl or hydrophobic sequence of 8 to 20 carbons and the combination of such peptides with lipids in a synthetic lung surfactant which is medicinally effective in the treatment of respiratory distress syndromes. The composition of the present invention may be prepared in high purity and in a standardized fashion as it is a defined mixture of synthetic components. Also, the components are not derived from animal sources which minimizes the risk of contamination by viruses and bacteria.

BRIEF DESCRIPTION OF THE TABLES

Table I shows the results from amino acid analysis of the synthesized peptides.

Table II shows the results of pressure-volume experiments showing the effectiveness of compounds in the adult rat lung model.

SUMMARY OF THE INVENTION

The present invention comprises synthetic lung surfactants consisting of a polypeptide of formula 1:

$$X—A_1—A_2—A_3—A_4—Y \qquad 1$$

or an optically active isomer or pharmaceutically acceptable salt thereof; wherein
X is an acyl or alkyl group of 8 to 18 carbon atoms
Y is —OH or —NH$_2$;
$A_1$ is a bond or negatively charged amino acid selected from Glu or Asp;
$A_2$ is a hydrophobic amino acid selected from Trp, Tyr, Phe, His, Val, Leu, or Ile;
$A_3$ is Aib, Glu, Gln, Leu, Ala, Orn or a bond; and
$A_4$ is a positive charged amino acid selected from Lys, Arg or His;
wherein, when $A_3$ is a bond, $A_1$ and $A_2$ may be interchanged;
which optionally may be associated with a lipid wherein the lipid is comprised of one or more of the type associated with natural pulmonary surfactant.

The present invention further comprises synthetic lung surfactants consisting of a polypeptide of formula 2:

$$X—A_1—A_2—A_3—A_4—Y \qquad 2$$

or an optically active isomer or pharmaceutically acceptable salt thereof; wherein
X is an acyl or alkyl group of 8 to 18 carbon atoms
Y is —OH or —NH$_2$;
$A_1$ is a bond or negatively charged amino acid selected from Glu or Asp;
$A_2$ is a hydrophobic amino acid selected from Trp, Tyr, Phe, His, Val, Leu, or Ile;
$A_3$ is Aib, Glu, Gln, Leu, Ala, Orn or a bond; and
$A_4$ is a positive charged amino acid selected from Lys, Arg or His;
which optionally may be associated with a lipid wherein the lipid is comprised of one or more of the type associated with natural pulmonary surfactant.

The present invention further comprises synthetic lung surfactant consisting of polypeptide of formula 3

$$X—A_1—A_2—A_3—A_4—Y \qquad 3$$

or an optically active isomer or pharmaceutically acceptable salt thereof, wherein:
X is an acyl or akyl group of 8 to 18 carbon atoms;
Y is —OH or —NH2;
$A_1$ is a bond, Glu, or Asp;
$A_2$ is Trp, Glu, or Asp;
$A_3$ is a bond, Aib, Glu, Gln, Leu, Ala or Orn; and
$A_4$ is Lys, or Arg;
which optionally may be associated with a lipid wherein the lipid is comprised of one or more of the type associated with natural pulmonary surfactant.

These peptides and peptide-lipid complexes and their pharmaceutical compositions are useful in treating mammalian respiratory distress syndrome.

DETAILED DESCRIPTION OF THE INVENTION

The following common abbreviations of the naturally occurring amino acids are used throughout this specification:
Ala or A—alanine
Val or V—valine
Leu or L—leucine
Ile or I—isoleucine
Phe or F—phenylalanine
Trp or W—tryptophan
Met or M—methionine
Ser or S—serine
Tyr or Y—tyrosine
Asp or D—aspartic acid
Glu or E—glutamic acid
Gln or Q—glutamine
Lys or K—lysine
Arg or R—arginine
Aib—amino-isobutyric acid
Orn—ornithine The natural amino acids, with the exception of glycine, contain a chiral carbon atom. Unless otherwise specifically indicated, the optically active amino acids, referred to herein, are of the L-configuration. As is customary, the structure of peptides written out herein issuch that the amino terminal end is on the left side of the chain and the carboxy terminal end is on the right side of the chain.

The N-terminal amino acid is covalently bonded through the N-amino group to an acyl or alkyl group of 8 to 18 carbon atoms. An acyl group of from 8 to 18 carbon atoms is taken to include straight, branched, cyclic, saturated and unsaturated acyl groups having 1 or 2 carbonyl moieties per group. An alkyl group is taken to include straight, branched, or cyclic alkyl groups. Synthesis of the N-acyl peptides is known by those skilled in the art. Synthesis is generally accomplished by an activated acyl acid as the corresponding ester or through the acyl anhydride reacted with the N-amino group of the peptide, e.g., N-hydroxybenzotriazole ester (HOBT ester). The acyl or aklyl chain increases the lipid binding affinities of the peptides.

As used herein the term "hydrophobic amino acid" means a nonpolar residue with an aliphatic hydrocarbon side chain such as Val, Leu or Ile; or a nonpolar residue with an aromatic group such as Phe, Tyr, Trp or His.

As used herein the term "negatively charged amino acid" means a polar residue with an acidic hydrophilic side chain such as Glu or Asp.

As used herein the term "positive charged amino acid" means a polar residue with a basic hydrophilic side chain such as Lys, Arg or His.

These small synthetic peptides, with sequences unrelated to any region within the known lung surfactant proteins, and attached alkyl or acyl groups in combination with pure DPPC, restore quasi-static lung compliance in vitro.

Also preferred are those polypeptides of formula 1 wherein the substituents can be independently selected to form a preferred grouping of substituents from the listed peptides below.

Palmitoyl-Glu—Trp—Ala—Lys—NH$_2$ (SEQ ID NO: 1)
Palmitoyl-Glu—Trp—Gln—Lys—NH$_2$ (SEQ ID NO: 2)
Palmitoyl-Glu—Trp—Glu—Lys—NH$_2$ (SEQ ID NO: 3)
Palmitoyl-Glu—Trp—Leu—Lys—NH$_2$ (SEQ ID NO: 4)
Palmitoyl-Glu—Trp—Aib—Lys—NH$_2$ (SEQ ID NO: 5)
Palmitoyl-Trp—Glu—Lys—NH (SEQ ID NO: 6)
Octanoyl-Glu—Trp—Aib—Lys—NH$_2$ (SEQ ID NO: 7)

Additionally applicants prefer those polypeptides of formula 1 wherein independently Y is selected to be an amino group and/or X is palmitoyl. The optimal peptide contains a tryptophan residue at the A$_2$ position, but may accommodate Glu. The A$_4$ position optimally accommodates Lys. Further, within the substituents of A$_1$, A$_2$, A$_3$, and A$_4$, amino acids and bonds can be independently selected to form a more preferred grouping of substituents.

The polypeptides of this invention can be prepared by a variety of procedures readily known to those skilled in the art. Such procedures include solid phase sequential synthesis. The solid phase sequential procedure can be performed using established automated methods such as by use of the ABI peptide synthesizer. In this procedure an α-amino protected amino acid is bound to a resin support. The resin support employed can be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced α-amino protected amino acid.

An example of a hydroxymethyl resin is described by Bodanszky, et al., *Chem. Ind. (London)* 38, 1597–98 (1966). A chloromethylated resin is commercially available from Bio Rad Laboratories, Richmond, Calif. and the preparation of such a resin is described by Stewart, et al., "Solid Phase Peptide Synthesis" (Freeman & Co., San Francisco 1969), Chapter 1, pp. 1–6. The protected amino acid can be bound to the resin by the procedure of Gisin, *Helv. Chem. Acta,* 56, 1476 (1973). Many resin bound, protected amino acids are commercially available. As an example, to prepare a polypeptide of this invention wherein the carboxy terminal end is a Lys residue, a tert-butyloxycarbonyl (Boc) protected Lys bound to a benzylated, hydroxymethylated phenylacetamidomethyl (PAM) resin can be used and is commercially available.

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and γ-chlorobutyryl; (2) aromatic urethan type protecting groups such as benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl, 1-(p-biphenyl)-1-methylethoxycarbonyl, α,α-dimethyl-3,5-dimethoxybenzyloxycarbonyl and benzhydryloxycarbonyl; (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; (7) trialkylsilane groups such as trimethylsilane. The preferred α-amino protecting group is tert-butyloxycarbonyl.

The selection of an appropriate coupling reagent is within the skill of the art. A particularly suitable coupling reagent where the amino acid to be added is Gln, Asp or Arg is N,N'-diisopropylcarbodiimide and 1-hydroxybenzotriazole. The use of these reagents prevents nitrile and lactam formation. Other coupling agents are (1) carbodiimides (e.g., N,N'-dicyclohexylcarbodiimide and N-ethyl-N'-(γ-dimethylaminopropylcarbodiimide); (2) cyanamides (e.g., N,N-dibenzylcyanamide); (3) ketenimines; (4) isoxazolium salts (e.g., N-ethyl-5-phenyl isoxazolium-3'-sulfonate; (5) monocyclic nitrogen containing heterocyclic amides of aromatic character containing one through four nitrogens in the ring such as imidazolides, pyrazolides and 1,2,4-triazolides. Specific heterocyclic amides that are useful include N,N'-carbonyldiimidazole and N,N'-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., (Boc-Arg)$_2$-O) and (8) nitrogen containing heterocyclic compounds having a hydroxy group on one ring nitrogen (e.g., N-hydroxyphthalimide, N-hydroxysuccinimide and 1-hydroxybenzotriazole). Other activating reagents and their use in peptide coupling are described by Kapoor, *J. Pharm. Sci.,* 59, pp. 1–27 (1970). Applicant prefers the use of symmetrical anhydride as a coupling reagent.

Each protected amino acid or amino acid sequence is introduced into the solid phase reactor in about a four-fold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser, et al., *Analyt. Biochem.* 34, 595 (1970).

After the desired amino acid sequence has been obtained, the peptide is removed from the resin. This can be done by methanolysis such as by treatment of the resin bound polypeptide with a solution of dimethyl sulfide, p-cresol and thiocresol in dilute aqueous hydrofluoric acid.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed by cleavage during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxycarbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The preferred protecting group is benzyl.

These groups are removed by procedures well known in the art. Typically protecting group removal is done after the peptide chain synthesis is complete but the protecting groups can be removed at any other appropriate time.

The polypeptides of Formula 1 can form pharmaceutically acceptable salts with any non-toxic, organic or inorganic acid. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower) alkylpiperidine, and any other suitable amine.

The phospholipids of the protein-phospholipid complexes of this invention can be any phospholipid and this term as used herein includes the phosphoglycerides and the sphingolipids. Phosphoglycerides are those di-fatty acid esters of glycerol in which the remaining hydroxy group, a terminal hydroxy group, of the gylcerol moiety forms an ester with phosphoric acid. Commonly the phosphoric acid moiety of the phosphoglycerides forms a second ester with an alcohol such as ethanolamine, serine, choline, or glycerol. Sphingolipids are those mono-fatty acid esters of sphingosine or dihydrosphingosine in which the hydroxy group at the 1-position forms an ester with the choline ester of phosphoric acid. The preferred lipids of the protein-phospholipid complexes of this invention comprise dipalmitoylphosphatidylcholine (DPPC), phosphatidylcholine molecules containing acyl chains of other lengths and degrees of saturation (PC), cardiolipin (CL), phosphatidylglycerols (PG), phosphatidylserines (PS), fatty acids (FA), and triacylglycerols (TG). DPPC comprises the major component of the lung surfactant mixture while PC, CL, PG, PS, FA, and TG comprise minor components. Suitable fatty acids for use in the phospholipids of this invention are long chain carboxylic acids (generally having eight or more carbon atoms), typically unbranched. The fatty acids can be either saturated or unsaturated. Representative fatty acids are lauric, myristic, palmitic, and oleic acids.

Pharmaceutical preparations of the protein-phospholipid complexes of this invention can be prepared as a dry mixture or in an aqueous suspension, in some instances containing small amounts of organic solvents, such as, for example, ethanol or trifluoroethanol, detergents, such as, for example, sodium dodecyl sulfate or sodium deoxycholate, salts, such as calcium chloride or sodium chloride, carbohydrates, such as glucose, dextrose or mannitol, and amino acids, such as glycine and alanine. Where the pharmaceutical composition is made into liquid form, stabilizers, preservatives, osmotic pressure regulators, buffering agents, and suspending agents of the liquid may be added. If desired, suitable germicides may also be added. The pH of the aqueous suspension may vary between 2 and 10 and may be adjusted with acids and bases, such as, for example, hydrochloric acid, sodium phosphate, or sodium hydroxide. The dry mixture may be reconstituted in an aqueous solution containing pharmaceutically acceptable salts, organic solvents, and detergents. The aqueous preparation may be dialyzed, filtered, or chromatographed to exchange the suspending medium with a pharmaceutically acceptable medium prior to use. The preparation may be administered as a dry powder, an aqueous suspension, or as an aerosol directly into the lungs of the distressed subject. The pharmaceutical composition of the present invention may be charged in hermetically sealed containers such as vials and ampules and be preserved sterilely. The composition may be stored in a vial or ampule separately from a vial or ampule containing the suspension buffer and the dry or hydrated composition may be mixed with the suspension buffer prior to use.

Lipid constitutes from 50 to 99.9% of the lung surfactant preparation. Suitable lipids include dipalmitoylphoshatidylcholine (DPPC), phosphitidylcholine (PC), cardiolipin (CL), phosphitidyl glycerol (PG), phosphitidyl serine (PS), fatty acid (FA), and triglyceride (TG.) DPPC comprises the major lipid species and is present in concentrations of 60 to 100% of the total lipid weight. The remaining lipids are present in minor concentrations. PC, CL, PG and PS may comprise up to 30% of the lipids, and FA and TG may comprise up to 10% of the lipid weight. The fatty acyl chains of the minor lipid components may be saturated or unsaturated and of any chain length. Chain lengths of 12 to 16 carbon atoms and up to 2 unsaturated bonds are preferred. The preferred lipid composition is 85–100% DPPC plus 0–15% of PG. Most preferred is pure DPPC.

The lipid components of the synthetic lung surfactant are commonly found in mammalian lung surfactant and are available from common industrial sources in high purity. The polypeptide components are prepared by solid-phase peptide synthesis by methods familiar to those skilled in the art. Mixtures of the lipids of the invention with proteins isolated from mammalian lung lavage have been shown to be effective in treating neonatal RDS. However, mixtures of these lipids with synthetic peptides in lung surfactant preparations have only recently been reported (McLean, et al. (1992) Am. J. Physiol., L292–L300; Waring, et al. (1989) Peptide Research 2(5), 308–313; Cochrane, et al. (1991) Science 254, 566–68).

Lipids are suspended as liposomes by methods familiar to one skilled in the art wherein they are mixed in a volatile organic solvent or mixtures of solvents, such as mixtures of chloroform and methanol. The organic solvent is removed by evaporation under nitrogen, argon, or under vacuum. An aqueous solution which may contain organic and inorganic acids, bases, and salts, and saccharides such as dextrose is added to the dry lipid mixture to attain a final concentration of 0.1 to 100 mg of DPPC per ml. In general, it is preferable, but not necessary to warm the mixture to 35°–50° C., mix vigorously, and incubate for up to 2 hours at 25°–50° C. Then, peptide or a mixture of peptides is added as a dry powder or suspended in an aqueous solution in some cases containing a suitable organic solvent, such as ethanol or trifluorethanol, or a denaturing agent, such as guanidinium hydrochloride or urea, which improves the solubility of the peptide in the aqueous suspension. Association of peptide and lipid may be promoted at a particular pH, thus the pH of the aqueous solution may vary from 2 to 10. The preferred method for mixing peptide and lipid is to add dry peptide to lipid in water at 45°–50° C. and to mix by bath ultrasonication at 45°–50° C. for 30–90 minutes, then freeze-dry and store at −20° C.

Alternatively, lipids and peptides are mixed in a volatile organic solvent with or without a small amount of water. The volatile solvent is evaporated under a stream of nitrogen or argon, in a vacuum oven, or by rotary evaporation either before or after addition of an aqueous solvent.

The mixture of lipid and peptide prepared by one of the methods described above is incubated for up to 2 hours, preferably at 35°–50° C. with sonic irradiation. The mixture may then be dialyzed, filtered, or chromatographed to replace the aqueous medium with a pharmaceutically acceptable medium, although this is not necessary. The mixture may then be lyophilized or aerosolized.

The polypeptide-phospholipid complexes of this invention can be used in the treatment of adult and neonatal respiratory distress syndromes. The complexes of this invention when administered to RDS patients, act as synthetic pulmonary surfactants and either replace the natural, missing surfactant or augment the lack of sufficient natural surfactant. Treatment is continued until the infant's lungs produce a sufficient amount of natural, pulmonary surfactant so as to render further treatment unnecessary, generally when normal gas exchange is achieved.

The preparations are preferably those suitable for endotracheal administration, that is as a liquid suspension, a dry powder, or an aerosol. For a liquid suspension, the dry mixture or the mixture in aqueous suspension is mixed with suitable agents, such as water, saline solutions, dextrose, and glycerol to produce a pharmaceutically effective composition. Preferred liquid suspensions will contain 0.8 to 1.0 weight percent of sodium chloride and will be 1–20 mM in calcium ion. The preparation is then filter sterilized. In general, the preparation comprises 1 to 100 mg of DPPC per ml and is administered at a dose of 0.2 to 5 ml/kg. To prepare a dry mixture, the aqueous suspension is lyophilized. The aerosol is prepared from a finely divided dry powder suspended in a propellant, such as lower alkanes and fluorinated alkanes, such as Freon. The aerosol is stored in a pressurized container.

The surfactant is administered, as appropriate to the dosage form, by endotracheal tube, by aerosol administration, or by nebulization of the suspension or dry mixture into the inspired gas. The surfactant is administered in one or multiple doses of 10 to 200 mg/kg. The preferred method of administration is as a suspension of peptide and lipid in physiological saline solution at a concentration of 5–10 mg of surfactant per ml through an endotracheal tube, achieving a dose of 50–100 mg/kg.

The polypeptide of the present invention is administered to treat a subject. "Subject" means a mammal, for example, but not limited to, a human being.

EXAMPLE 1

Experimental Chemical Procedures

Peptide Synthesis and other Chemicals. Peptides were synthesized on a 0.5 mmol scale by solid-phase methods on an Applied Biosystems Inc. (Foster City, Calif.) Model 430-A peptide synthesizer. p-methylbenzoxyhydrylamine (pMBHA) resin was used to give C-terminal amides on cleavage. Na-t-Boc (t-butyloxycarbonyl) amino acids with side chain protection Cys(ethylthio), Glu(benzyl) and Lys (2-chlorobenzyloxycarbonyl) from Peptides International were double-coupled via their preformed symmetrical anhydrides. The acyl group, i.e.,palmitoyl and octyl, was coupled by activating the acid to form the symmetrical anhydride. Nα-t-Boc groups were removed with 50% trifluoroacetic acid (TFA) in methylene chloride and neutralized with 10% diisopropylethylamine (DEA) in dimethyl formamide. The peptides were cleaved from the resin and deprotected in anhydrous HF containing 5% anisole and 5% dimethyl sulfide at −5° C. for 45 min. HF was removed in vacuo and the peptide extracted from the resin with 50% aqueous acetonitrile. The combined extracts were frozen and lyophilized and purified by reverse phase preparative HPLC on a Rainin Dynamax (21.4×250 mm) $C_{18}$ column at 40 mL/min with an acetonitrile gradient in 0.1% aqueous TFA (pH 2) monitored at 214 nm. The major peak was collected and lyophilized. The purity (>97%) and identity of the synthetic peptides were confirmed by a single peak in the analytical high performance liquid chromatogram (HPLC), capillary zone electrophoresis, fast-atom bombardment mass spectrometry (FAB-MS) on a VG Analytical ZAB2-SE which gave single molecular ions consistent with the correct sequences, and amino acid analyses which were within 10% of the predicted values for each residue. L-α-dipalmitoylphosphatidylcholine (DPPC) (>99% pure) was from Avanti Polar Lipids (Birmingham, Ala.). Using these procedures the following peptides were synthesized; their analytical properties are found in Table 1.

1. Palmitoyl—Glu—Trp—Ala—Lys—$NH_2$ (SEQ ID NO: 1)
2. Palmitoyl—Glu—Trp—Gln—Lys—$NH_2$ (SEQ ID NO: 2)

3. Palmitoyl—Glu—Trp—Glu—Lys—NH$_2$ (SEQ ID NO: 3)
4. Palmitoyl—Glu—Trp—Leu—Lys—NH$_2$ (SEQ ID NO: 4)
5. Palmitoyl—Glu—Trp—Aib—Lys—NH$_2$ (SEQ ID NO: 5)
6. Palmitoyl—Trp—Glu—Lys—NH2 (SEQ ID NO: 6)
7. Octanoyl—Glu—Trp—Aib—Lys—NH$_2$ (SEQ ID NO: 7)

TABLE 1

FABS-MASS SPECTROMETRY ANALYSIS OF PEPTIDES 1–7

| MDL # | PEPTIDE | FAB MS | AAA |
|---|---|---|---|
| 102,319 | Palmitoyl—Glu—Trp—Ala—Lys—NH$_2$ | [M + H]+ = 770.4 | @ 74.9% |
| 102,697 | Palmitoyl—Glu—Trp—Gln—Lys—NH$_2$ | [M + H]+ = 827.4 | @ 68.8% |
| 101,459 | Palmitoyl—Glu—Trp—Glu—Lys—NH$_2$ | [M + H]+ = 828.5 | @ 71.9% |
| 101,447 | Palmitoyl—Glu—Trp—Leu—Lys—NH$_2$ | [M + H]+ = 812.7 | @ 75.9% |
| 102,720 | Palmitoyl—Glu—Trp—Aib—Lys—NH$_2$ | [M + H]+ = 784.4 | @ 43.9% |
| 102,739 | Palmitoyl—Trp—Glu—Lys—NH$_2$ | [M + H]+ = 699.5 | @ 71.3% |
|  | Palmitoyl—Glu—Trp—Aib—Lys—NH$_2$ | [M + H]+ = 672.4 | @ 62.9% |

BIOLOGICAL PROPERTIES

Example 2

Preparation of Artificial Surfactants

Preparation of Artificial Surfactants. For triplicate samples of the synthetic lung surfactants 75 mg of DPPC (L-α-dipalmitoylphosphatidylcholine; >99% pure; Avanti Polar Lipids, Birmingham, Ala.) in 1 ml of chloroform were dried under a stream of nitrogen and placed in a lyophilizer overnight to remove traces of organic solvent. To the dry lipid mixture were added 9 ml of water. The preparation was incubated for 1 hr at 45°–50° C. with occasional vortexing. Then, in some samples, 1.5 mg of dry test peptide were added to the aqueous preparation. The preparations were mildly sonicated with and without peptide in a cleaning bath sonicator (Branson 1200) at 45°–50° C. for 2 h to promote peptide dispersion and peptide-lipid interactions. The resulting lipid-peptide mixtures were divided into three parts, lyophilized and stored at −20° C.

Preparation of DPPC Complex of Palmitoyl-Glu—Trp—Ala—Lys—NH$_2$ (SEQ ID NO: 1)

Peptide 1 was prepared by solid-phase synthesis. DPPC (25 mg) in 1 ml of chloroform was dried under a stream of nitrogen and lyophilized to remove traces of organic solvent. To the dry lipid mixture was added 9 ml of water. The preparation was incubated for 1 hour at 45° C. Then, 1.5 mg of dry Peptide I was added to the aqueous preparation. The preparation was sonicated in a bath ultrasonicator at 45° C. for 2 hours. The resulting lipid-peptide mixture was lyophilized and stored at 4° C. for up to one month. The preparation was incubated for 1 hour at 45° C. with periodic mixing. The preparation has a translucent white appearance and is somewhat less turbid than DPPC alone.

Preparation of DPPC Complex of Palmitoyl-Glu—Trp—Gln—Lys—NH$_2$ (SEQ ID NO: 2)

Peptide 2 was prepared by solid-phase synthesis and mixed with DPPC as described under Example I.

Preparation of DPPC Complex of Palmitoyl-Glu—Trp—Glu—Lys—NH$_2$ (SEQ ID NO: 3)

In a like manner, the Peptide 3 was prepared and its complex with DPPC was formed.

Preparation of DPPC Complex of Palmitoyl-NH$_2$ (SEQ ID NO: 4)

In a like manner, the Peptide 4 was prepared and its complex with DPPC was formed.

Preparation of DPPC Complex of Palmitoyl-Glu-Trp-Aib-Lys-NH23 (SEQ ID NO: 5)

In a like manner, the Peptide 5 was prepared and its complex with DPPC was formed.

Preparation of DPPC Complex of Palmitoyl-NH2 (SEQ ID NO: 6)

In a like manner, the Peptide 6 was prepared and its complex with DPPC was formed.

Preparation of DPPC Complex of Octanoyl-NH$_2$ (SEQ ID NO: 7)

In a like manner, the Peptide 7 was prepared and its complex with DPPC was formed.

EXAMPLE 3

Isolated Rat Lavaged Lung Model

The experimental procedures for animal preparation, pressure-volume curve registration and lung lavage have been described by the rat lung model (Ikegami, et al., (1979) *Pediatr. Res.* 13, 777–780) as modified by McLean et al., *Am. J. Physiol.* (1992), L292–L300. Briefly, the lungs of adult rats were suspended in 0.9% saline at 37° C. were connected to a water manometer and an air-filled syringe by a T-tube. The deflation limb of a pressure-volume curve was recorded prior to lavage, after extensive lavage with 0.9% NaCl, 10 mM HEPES, pH 7.4 and after administration of surfactant mixtures in 2 ml of 0.9% NaCl, 10 mM HEPES buffer, pH 7.40. The deflation limbs of the pressure-volume (P-V) curves in adult rat lungs were analyzed by calculating the total lung capacities (% TLC) at 5 and 10 cm H$_2$O pressure (PC5 and PC10). The per cent of total lung capacities at 5 and 10 cm of H$_2$O (PC$_5$ and PC$_{10}$) were measured after addition of the synthetic lung surfactants to adult rat lavaged lungs at a dose of 25 mg of lipid (32 umoles) and 1 mg of peptide. Restorations are based on PC$_5$. Values are mean ±S.E. Significantly different from deficient at p<0.05. Comparisons were based on restoration, i.e. for PC$_5$, (PC$_{5(sufficient)}$ −PC$_{5(test)}$)×100%/(PC$_{5(sufficient)}$ −PC$_{5(deficient)}$) and made by one-way analysis of variance using the GLM procedure with specific contrasts of the means (SAS Institute Inc., Cary, N.C.). Lavage and treatment with test mixtures did not produce a change in the absolute TLC of greater than 6%.

TABLE II

Efficacy of Natural and Synthetic Surfactants in the Adult Rat Lavaged Lung Model

| Mixture | n | $PC_5$ (% TLC) | $PC_{10}$ (% TLC) | Restoration (%) |
|---|---|---|---|---|
| Sufficient Lungs | 50 | 68 ± 1 | 87 ± 1 | 100 |
| Deficient Lungs 50 | | 17 ± 1 | 45 ± 1 | O |
| Reference II | 3 | 56 ± 3 | 79 ± 2 | 77 ± 5 |
| Reference I | 4 | 13 ± 1 | 31 ± 2 | −11 ± 8 |
| Seq ID No: 1 + DPPC | 2 | 53 ± 5 | 75 ± 5 | 79 ± 11 |
| Seq ID No: 2 + DPPC | 2 | 49 ± 1 | 71 ± 4 | 73 ± 6 |
| Seq ID No: 3 + DPPC | 2 | 50 ± 3 | 73 ± 2 | 73 ± 5 |
| Seq ID No: 4 + DPPC | 2 | 43 ± 4 | 66 ± 3 | 66 ± 10 |
| Seq ID No: 5 + DPPC | 1 | 35 | 57 | 33 |
| Seq ID No: 6 + DPPC | 2 | 50 ± 2 | 72 ± 2 | 69 ± 4 |
| Seq ID No: 7 + DPPC | 2 | 28 ± 6 | 55 ± 5 | 23 ± 9 |

References, consisting of DPPC alone and dog lung surfactant, respectively, were employed as reference standards: Reference I was prepared as follows. DPPC was purchased from Avanti Polar Lipids. 25 mg of DPPC in chloroform was dried under a stream of nitrogen and lyophilized to remove traces of organic solvent. To the dry lipid mixture was added 3 ml of water. The preparation was incubated at 45° C. for 1 hour with ultrasonication in a bath sonicator. The lipid was lyophilized, stored at 4° C. for up to one week and mixed with 9 ml of 0.9% NaCl, 20 mM HEPES buffer, pH 7.40. After periodic mixing during incubation at 45° C. for 1 hour Reference I was tested in the adult rat lung model. Reference I has no effect on improving the compliance of the rat lung and is ineffective as a lung surfactant Reference II was prepared as follows. Dog lung surfactant was prepared by methods familiar to those in the art. Reference II restores the lung capacity at 5 cm water to >75% of the fully sufficient rat lung.

What is claimed is:

1. A polypeptide of the formula:

$$X-A_1-A_2-A_3-A_4-Y$$

or an optically active isomer or pharmaceutically acceptable salt thereof; wherein X is an acyl or alkyl group of 8 to 18 carbon atoms;
Y is —OH or —NH$_2$;
A$_1$ is a bond, Glu or Asp;
A$_2$ is Trp, Tyr, Phe, His, Val, Leu, or Ile;
A$_3$ is Aib, Glu, Gln, Leu, Ala, Orn, or a bond; and
A$_4$ is Lys, Arg, or His;
wherein, when A$_3$ is a bond, A$_1$ and A$_2$ may be interchanged;
which optionally may be associated with a lipid wherein the lipid is comprised of one or more of the type assoicated with natural pulmonary surfactant
with the proviso that when A$_1$ is a bond or Glu; A$_2$ is Trp; A$_3$ is Aib, Glu, or Ala; and A$_4$ is Lys, X is not an aromatic acyl.

2. A polypeptide of the formula:

$$X-A_1-A_2-A_3-A_4-Y$$

or an optically active isomer or pharmaceutically acceptable salt thereof; wherein X is an acyl or alkyl group of 8 to 18 carbon atoms;
Y is —OH or —NH$_2$;
A$_1$ is a bond, Glu or Asp;
A$_2$ is Trp, Tyr, Phe, His, Val, Leu, or Ile;
A$_3$ is Aib, Glu, Gln, Leu, Ala, Orn, or a bond; and
A$_4$ is Lys, Arg, or His;
which optionally may be associated with a lipid wherein the lipid is comprised of one or more of the type assoicated with natural pulmonary surfactant;
with the proviso that when A$_1$ is a bond or Glu; A$_2$ is Trp; A$_3$ is Aib, Glu, or Ala; and A$_4$ is Lys, X is not an aromatic acyl.

3. A polypeptide of the formula:

$$X-A_1-A_2-A_3-A_4-Y$$

or an optically active isomer or pharmaceutically acceptable salt thereof; wherein X is an acyl or alkyl group of 8 to 18 carbon atoms;
Y is —OH or —NH$_2$;
A$_1$ is a bond, Glu or Asp;
A$_2$ is Trp, Glu or Asp;
A$_3$ is Aib, Glu, Gln, Leu, Ala, Orn-X, or a bond; and
A$_4$ is Lys or Arg;
which optionally may be associated with a lipid wherein the lipid is comprised of one or more of the type assoicated with natural pulmonary surfactant;
with the proviso that when A$_1$ is a bond or Glu; A$_2$ is Trp; A$_3$ is Aib, Glu, or Ala; and A$_4$ is Lys, X is not an aromatic acyl.

4. A polypeptide as in one of claims 1–3, in which A$_1$ is Glu.

5. A polypeptide as in one of claims 1–3, in which A$_2$ is a Trp.

6. A polypeptide as in one of claims 1–3, in which A$_3$ is a Leu.

7. A polypeptide as in one of claims 1–3, in which A$_4$ is a Lys.

8. A polypeptide as in one of claims 1–3, in which X is palmitoyl.

9. A polypeptide as in one of claims 1–3, in which Y is —NH$_2$.

10. A polypeptide as in one of claims 1–3 which is Palmitoyl-Glu-Trp-Ala-Lys-NH$_2$ (SEQ ID NO: 1).

11. A polypeptide as in one of claims 1—3 which is Palmitoyl-Glu-Trp-Gln-Lys-NH$_2$ (SEQ ID NO: 2).

12. A polypeptide as in one of claims 1–3 which is Palmitoyl-Glu-Trp-Glu-Lys-NH$_2$ (SEQ ID NO: 3).

13. A polypeptide as in one of claims 1–3 which is Palmitoyl-Glu-Trp-Leu-Lys-NH$_2$ (SEQ ID NO: 4).

14. A polypeptide as in one of claims 1–3 which is Palmitoyl-Glu-Trp-Aib-Lys-NH$_2$(SEQ ID NO: 5).

15. A polypeptide as in one of claims 1–3 which is Palmitoyl-Trp-Glu-Lys-NH$_2$ (SEQ ID NO: 6).

16. A polypeptide as in one of claims 1–3 which is Octanoyl-Glu-Trp-Aib-Lys (SEQ ID NO: 7).

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear     ( i i ) MOLECULE TYPE: peptide     ( i x ) FEATURE:
        ( A ) NAME/KEY: Modified-site
        ( B ) LOCATION: 1
        ( D ) OTHER INFORMATION: /note= "Xaa = N-alpha- palmityl-glutamic acid (palmityl-Glu)"

( i x ) FEATURE:
        ( A ) NAME/KEY: Modified-site
        ( B ) LOCATION: 4
        ( D ) OTHER INFORMATION: /note= "Xaa = Lysin-1-amide ( L y s - N H 2 )"

( x i ) SEQUENCE DESCRIPTION: SEQ ID NO:1:

X a a   T r p   A l a   X a a
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear     ( i i ) MOLECULE TYPE: protein     ( i x ) FEATURE:
        ( A ) NAME/KEY: Modified-site
        ( B ) LOCATION: 1
        ( D ) OTHER INFORMATION: /note= "Xaa =

N-alpha- palmityl-glutamic acid (palmityl-Glu)"

( i x ) FEATURE:
   ( A ) NAME/KEY: Modified-site
   ( B ) LOCATION: 4
   ( D ) OTHER INFORMATION: /note= "Xaa = Lysin-1-amide
     ( L y s - N H 2 )"

( x i ) SEQUENCE DESCRIPTION: SEQ ID NO:2:

Xaa Trp Gln Xaa
1

( 2 ) INFORMATION FOR SEQ ID NO:3:

( i ) SEQUENCE CHARACTERISTICS:
   ( A ) LENGTH: 4 amino acids
   ( B ) TYPE: amino acid
   ( D ) TOPOLOGY: linear  ( i i ) MOLECULE TYPE: peptide  ( i x ) FEATURE:
   ( A ) NAME/KEY: Modified-site
   ( B ) LOCATION: 1
   ( D ) OTHER INFORMATION: /note= "Xaa =
     N-alpha- palmityl-glutamic acid (palmityl-Glu)"

( i x ) FEATURE:
   ( A ) NAME/KEY: Modified-site
   ( B ) LOCATION: 4
   ( D ) OTHER INFORMATION: /note= "Xaa = Lysin-1-amide
     ( L y s - N H 2 )"

( x i ) SEQUENCE DESCRIPTION: SEQ ID NO:3:

Xaa Trp Glu Xaa
1

( 2 ) INFORMATION FOR SEQ ID NO:4:

( i ) SEQUENCE CHARACTERISTICS:
   ( A ) LENGTH: 4 amino acids
   ( B ) TYPE: amino acid
   ( D ) TOPOLOGY: linear  ( i i ) MOLECULE TYPE: peptide  ( i x ) FEATURE:
   ( A ) NAME/KEY: Modified-site
   ( B ) LOCATION: 1
   ( D ) OTHER INFORMATION: /note= "Xaa =
     N-alpha- palmityl-glutamic acid (palmityl-Glu)"

( i x ) FEATURE:
   ( A ) NAME/KEY: Modified-site
   ( B ) LOCATION: 4
   ( D ) OTHER INFORMATION: /note= "Xaa = Lysin-1-amide
     ( L y s - N H 2 )"

( x i ) SEQUENCE DESCRIPTION: SEQ ID NO:4:

Xaa Trp Leu Xaa
1

( 2 ) INFORMATION FOR SEQ ID NO:5:

( i ) SEQUENCE CHARACTERISTICS:
   ( A ) LENGTH: 4 amino acids
   ( B ) TYPE: amino acid
   ( D ) TOPOLOGY: linear  ( i i ) MOLECULE TYPE: peptide  ( i x ) FEATURE:
   ( A ) NAME/KEY: Modified-site
   ( B ) LOCATION: 1

(D) OTHER INFORMATION: /note= "Xaa =
    N-alpha- palmityl-glutamic acid (palmityl-Glu)"

(ix) FEATURE:
    (A) NAME/KEY: Modified-site
    (B) LOCATION: 3
    (D) OTHER INFORMATION: /note= "Xaa =2-amino-isobutyric
        acid (Aib)"

(ix) FEATURE:
    (A) NAME/KEY: Modified-site
    (B) LOCATION: 4
    (D) OTHER INFORMATION: /note= "Xaa = Lysin-1-amide
        (Lys-NH2)"

(xi) SEQUENCE DESCRIPTION: SEQ ID NO:5:

Xaa Trp Xaa Xaa
1

(2) INFORMATION FOR SEQ ID NO:6:

(i) SEQUENCE CHARACTERISTICS:
        (A) LENGTH: 3 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa =
            N-alpha- palmityl-tryptophan (palmityl-Trp)"

(ix) FEATURE:
        (A) NAME/KEY: Modified-site
        (B) LOCATION: 3
        (D) OTHER INFORMATION: /note= "Xaa = Lysin-1-amide
            (Lys-NH2)"

(xi) SEQUENCE DESCRIPTION: SEQ ID NO:6:

Xaa Glu Xaa
1

(2) INFORMATION FOR SEQ ID NO:7:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa =
            N-alpha- octanoyl-glutamic acid (palmityl-Glu)"

(ix) FEATURE:
        (A) NAME/KEY: Modified-site
        (B) LOCATION: 3
        (D) OTHER INFORMATION: /note= "Xaa =2-amino-isobutyric
            acid (Aib)"

(ix) FEATURE:
        (A) NAME/KEY: Modified-site
        (B) LOCATION: 4
        (D) OTHER INFORMATION: /note= "Xaa = lysin-1-amide
            (Lys-NH2)"

(xi) SEQUENCE DESCRIPTION: SEQ ID NO:7:

Xaa Trp Xaa Xaa
1